United States Patent [19]

Silber

[11] Patent Number: 4,669,460
[45] Date of Patent: Jun. 2, 1987

[54] ANTI-ULCERATION BANDAGE

[76] Inventor: Arthur L. Silber, 543 Dobbins Dr., San Gabriel, Calif. 91775

[21] Appl. No.: 848,830

[22] Filed: Apr. 7, 1986

[51] Int. Cl.⁴ .............................................. A61B 19/00
[52] U.S. Cl. .................................................. 128/149
[58] Field of Search ................................ 128/149, 156

[56] References Cited

U.S. PATENT DOCUMENTS

| | | | |
|---|---|---|---|
| 2,864,362 | 12/1958 | Hermanson et al. | 128/156 |
| 3,253,861 | 5/1966 | Howard . | |
| 3,255,748 | 6/1966 | Wallerstein | 128/149 |
| 3,260,261 | 7/1966 | Gallovich | 128/149 |
| 3,266,064 | 8/1966 | Figman . | |
| 3,294,387 | 12/1966 | Chavannes . | |
| 3,392,081 | 7/1968 | Chavannes . | |
| 3,407,406 | 10/1968 | Werner et al. | 128/148 UX |
| 3,757,356 | 9/1973 | Freeman . | |
| 4,181,548 | 1/1980 | Weingarten . | |
| 4,225,989 | 10/1980 | Corbett et al. . | |
| 4,391,009 | 7/1983 | Schild et al. . | |
| 4,425,676 | 1/1984 | Crane . | |
| 4,541,136 | 9/1985 | Graebe . | |

FOREIGN PATENT DOCUMENTS

| | | | |
|---|---|---|---|
| 686613 | 7/1962 | Canada | 128/148 |
| 940840 | 6/1948 | France | 128/149 |

Primary Examiner—Gregory E. McNeill
Attorney, Agent, or Firm—William W. Haefliger

[57] ABSTRACT

An appliance used for transferring and distributing weight applied by a patient's body member, is disclosed. It includes:
(a) a first layer of synthetic flexible sheet material that forms a group of sealed, deformable air pockets distributed over layer area,
(b) and an attachment or attachments associated with that layer for removably attaching same to the body member in weight supporting relation.

12 Claims, 4 Drawing Figures

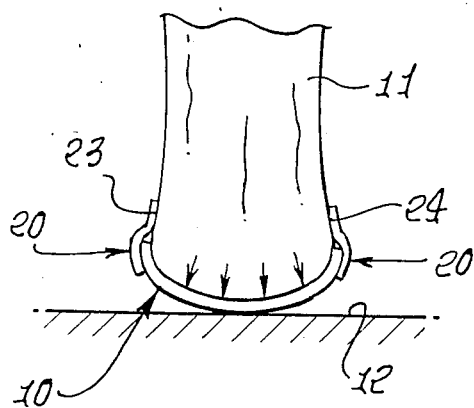
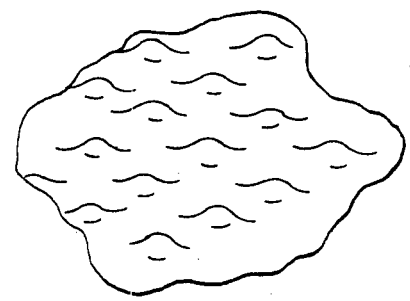
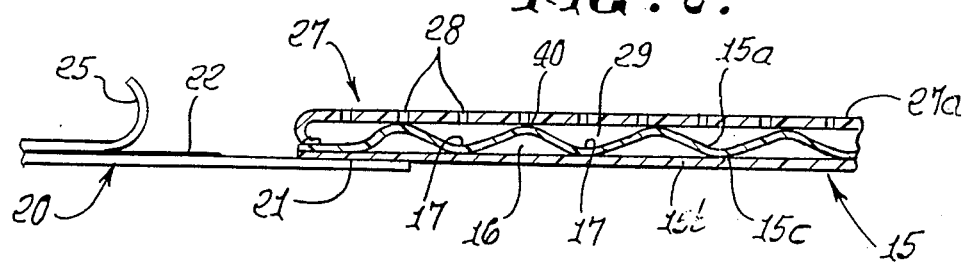
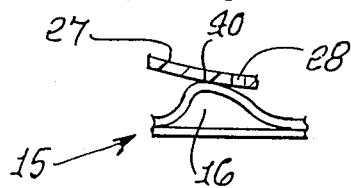
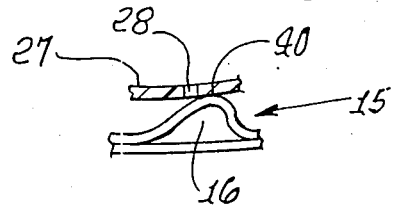
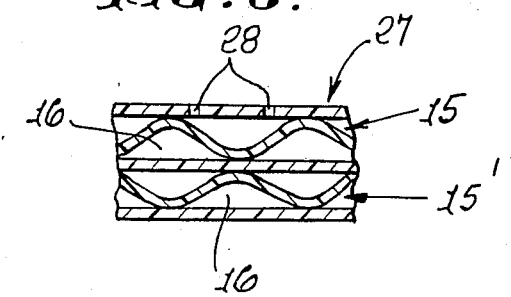
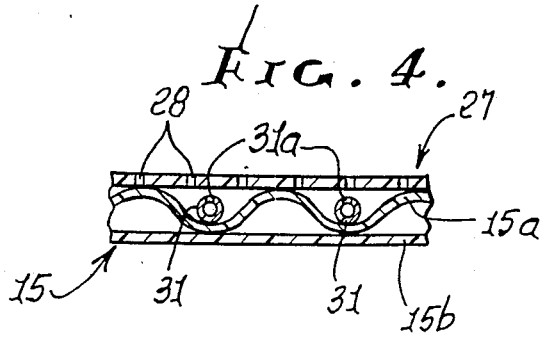

ANTI-ULCERATION BANDAGE

BACKGROUND OF THE INVENTION

This invention relates generally to the relief of local pressure application to the skin and flesh, as for example occurs with bed-ridden persons; more particularly it concerns the provision of a simple, effective appliance to accomplish this objective.

The problem of decubitus ulceration in bed-ridden people is serious and continuing and can lead to development of gangrene and other serious conditions. It requires, for example, frequent movement of patient's legs and arms by nursing personnel in hospitals and care centers to relieve cut-off circulation to pressure points developed by body weight transfer to support structure, bedding, and the like. There is need for an appliance which will minimize or eliminate deleterious pressure point development, so that such ulceration will not occur, despite minimal attention by nursing personnel.

SUMMARY OF THE INVENTION

It is a major object of the invention to provide an appliance or package which will meet the above described need. Basically, the appliance is used for transferring and distributing weight applied by a patient's body member (leg, foot, arm, etc.), and comprising (a) a first layer of synthetic flexible sheet material that forms a group of sealed, deformable, air pockets distributed over layer area, (b) and attachment means associated with said layer for removably attaching same to said body member in weight supporting relation thereto.

As will appear, the first layer may extend generally horizontally, and there may also be provided a second layer of air permeable flexible material extending generally horizontally above said first layer and closely associated therewith to transfer weight from the body member to the first layer, and to form therewith air zones which laterally communicate with the exterior and upwardly through said second layer. In this regard, the second layer typically forms "breathing " openings extending generally vertically through the second layer to provide air communication between the body member and said air zones.

Further aspects of the invention include the provison of another layer of the same construction as said first layer and extending generally parallel thereto at one side thereof; the provision of said (b) means in the form of adhesive material projecting peripherally outwardly of said first layer, for adhesive attachment to said body member; and the provision of duct means in zones between said air pockets for distributing treatment fluid thereto, and transfer to the supported body member.

These and other objects and advantages of the invention, as well as the details of an illustrative embodiment, will be more fully understood from the following specification and drawings, in which:

DRAWING DESCRIPTION

FIG. 1 is an elevation showing a body member supported by the weight distribution package of the invention;

FIG. 2 is an enlarged sectional elevation showing air pocket internal construction of a package incorporating the invention;

FIG. 2a is a fragmentary perspective view of air pocket forming sheet material in the package;

FIGS. 2b and 2c are sections showing air pocket deformations;

FIG. 3 is a view like FIG. 2, but showing a modified package construction; and

FIG. 4 is another view like FIG. 2, showing a further modified package construction.

DETAILED DESCRIPTION

FIG. 1 shows an appliance 10 in use to transfer and distribute weight applied by a patient's body member, as for example a foot 11 as shown (of a bed-ridden patient), or other member such as leg, arm, elbow, etc. The package distributes weight from a large area of the foot underside (see arrows) and transfer the weight to a support surface 12, as for example bed, table, etc. Therefore, pressure concentration to a small areal point of the body member is avoided, and blood circulation tends to be maintained instead of being interrupted by localized pressure application. The appliance is attached to the body member by means as at 20, to be further described, to enable the patient to move his foot or body member about, without destroying the functioning of the appliance.

A section in elevation through the appliance or package 10 appears as in FIG. 2 with the appliance detached from the body member so as to extend horizontally. As indicated, a first layer 15 of synthetic flexible sheet material forms a series of sealed, deformable air bubbles or pockets 16 distributed over the layer area. The plastic, film-like, sheet material may include upper and lower films 15a and 15b between which the air pockets 16 are formed, with valleys 17 between the vertical bulges formed by the pockets. The air pockets are isolated from one another by the valleys and by the film regions at 15c, where the upper and lower films merge, directly below the valleys. Therefore, the upwardly bulging air pockets receive imposition of body member weight at spaced crest locations 40 formed by the upper film 15a, and those crests 40 may shift about, laterally, as indicated in FIGS. 2b and FIG. 2c, as the body member moves about, turns slightly, etc. Accordingly, the multiple individual pressurized air pocket areas, receiving and distributing weight from the body member, themselves move about to continually vary the zones of multiple reverse pressure application to the body member as it is moved about, whereby additional relief from localized pressure to the body is achieved.

Also provided is attachment means associated with the first layer 15 for removably attaching same to the body member in weight supporting relation. Such means may comprise the plastic strip 20 peripherally attached to layer 15 at 21, and having adhesive material 22 thereon to adhere to the body as at 23 and 24 in FIG. 1. Protective sub-strips 25 covering the adhesive may be removed (as indicated in FIG. 2) to expose the active adhesive. Alternately, adhesive may be applied to the top surfaces 27a of layer 27, to adhere to the skin.

A further aspect of the invention is the provision of a second layer of air permeable flexible material extending generally horizontally above said first layer and closely associated therewith to transfer weight from the body member to the first layer, and to form therewith air zones which laterally communicate with the exterior and upwardly through said second layer. As shown in FIG. 2, such second layer 27 comprises a thin sheet of plastic material forming breathing openings 28 distributed over the second sheet, and extending vertically through same, i.e. between upper and lower sides thereof, to provide communication between the body member (i.e. the patients skin) and the air zones 29 formed by valleys between the upwardly bulging air pockets 15. Zones 29 typically communicate with the exterior laterally through a valley network, as appears in FIG. 2a, the air pockets being surrounded by the valleys. Thus, the patient's skin freely communicates with the exterior, and movement of his supported foot, ankle, leg, etc. achieves varied pressure application to the air pockets, so that breathing of virtually the entire supported skin area may be achieved. In this regard, the tops of the air pocket bulges need not be attached to sheet 27, only the peripheries of the sheets 15 and 27 may be attached, so that perforations 28 temporarily closed off by air pockets 16 will be re-opened to valleys 17, when the patient's body member is moved about.

FIG. 3 shows the provision of another layer 15' of the same construction as first layer 15, and extending generally horizontally and parallel thereto, as at the underside of the first layer. A double thickness air pocketed appliance is thereby achieved. The layers 15, 15' and 27 may be peripherally connected at spaced points indicated at 30, allowing air to circulate into and from the valleys described above.

FIG. 4 shows the provision of duct means, such as fluid ducts 31, in the air zones or valleys 16, for distributing treatment fluid to those zones. Note fluid distribution openings 31a in the ducts. Such fluid in then transferred to the patient's skin via said perforations 28 in layer 27, as under pressure applied to zones 16 (as by the patient's body member weight) to reduce the sizes of the zones 16 and/or by fluid pressure application via these ducts.

On usable material for layer 15 is known as "AIR CAP", a product of Sealed Air corporation.

I claim:

1. An appliance used for transferring and distributing weight applied by a patient's body member, comprising
   (a) a first layer of synthetic flexible sheet material that forms a group of sealed, deformable air pockets distributed over layer area,
   (b) and attachment means associated with said layer for removably attaching same to said body member in weight supporting relation thereto.

2. The appliance of claim 1 wherein said first layer extends generally horizontally and including
   (c) a second layer of air permeable flexible material extending generally horizontally above said first layer and closely associated therewith to transfer weight from the body member to the first layer, and to form therewith air zones which laterally communicate with the exterior and upwardly through said second layer.

3. The appliance of claim 2 wherein said second layer forms breathing openings extending generally vertically through the second layer to provide air communication between the body member and said air zones.

4. The appliance of claim 3 wherein said second layer comprises synthetic film.

5. The appliance of claim 1 including another layer of the same construction as said first layer and extending generally parallel thereto at one side thereof.

6. The appliance of claim 2 including another layer of the same construction as said first layer, and extending generally horizontally and parallel thereto, at the underside of the first layer.

7. The appliance of claim 1 wherein said (b) means comprises adhesive material projecting peripherally outwardly of said first layer, for adhesive attachment to said body member.

8. The appliance of claim 1 including duct means in zones betwen said air pockets for distributing treatment fluid thereto, and transfer to the supported body member.

9. The appliance of claim 2 including duct means in said air zones for distributing treatment fluid thereto, and for transfer to the supported body member via through perforations formed by said second layer.

10. The appliance of claim 1 including said body member to which said means is attached, said first layer extending in U-shaped configuration to conform to curvature of the supported underside of the body member.

11. The appliance of claim 3 wherein the first and second layers are connected to allow said perforations to variably communicate with said air zones as the body member is moved about.

12. The appliance of claim 2 wherein said attachment comprises adhesive on said second layer.

* * * * *